United States Patent [19]

Legendre et al.

[11] Patent Number: 6,030,602
[45] Date of Patent: Feb. 29, 2000

[54] PEPTIDE CONJUGATES FOR TRANSFECTING CELLS

[75] Inventors: Jean-Yves Legendre, Paris, France; Andreas Supersaxo, Basel, Switzerland; Arnold Trzeciak, Schopfheim, Germany

[73] Assignee: Hoffmann-La Roche Inc., Nutley, N.J.

[21] Appl. No.: 08/782,997

[22] Filed: Jan. 14, 1997

[30] Foreign Application Priority Data

Jan. 17, 1996 [EP] European Pat. Off. ............. 96100603

[51] Int. Cl.$^7$ .................... A61K 51/00; A61K 38/00; B32B 5/16; C07F 9/02
[52] U.S. Cl. ................ 424/1.69; 424/1.65; 428/402.2; 554/81; 530/324
[58] Field of Search ............................... 424/1.65, 1.69; 428/402.2; 554/81; 530/324

[56] References Cited

U.S. PATENT DOCUMENTS

| | | | |
|---|---|---|---|
| 4,429,008 | 1/1984 | Martin et al. | 428/402.2 |
| 5,169,933 | 12/1992 | Anderson et al. | 530/391.3 |
| 5,766,626 | 6/1998 | Gross | 424/450 |

FOREIGN PATENT DOCUMENTS 0727223  8/1996  European Pat. Off. .

OTHER PUBLICATIONS

The Merck Index, 12th Ed. Reg. No. 9967, Tyrocidine (1996).
The Merck Index, 12th Ed. Reg. No. 4552, Gramidicin S. (1996).
Vogler, et al., Helv. Chim. Acta, vol. 47, pp. 526–543, (See pp. 543–544 for English language summary) 1964.
Saberwal, et al. Cell–lytic and antibacterial peptides that act by perturbing the barrier function of membranes: facets of their conformational features, structure–function correlations and membrane–perturbing abilities, Biochimica et Biophysics Acta 1197, pp. 109–131 (1994).
Felgner, et al., Lipofection: A highly efficient, lipid–mediated DNA–transfection procedure, Proc. Natl. Acad. Sci. USA, vol. 84, pp. 7413–7417 (1987).
Ferderigos, et al., Synthesis of [A–2–αγ–Diaminobutyric Acid, A–19–Glutamic Acid] Sheep Insulin, J. Chem. Soc. Perkin Trans, vol. 11, pp. 1299–1305 (1977).

*Primary Examiner*—Ponnathapu Achutamurthy
*Assistant Examiner*—Peter P. Tung
*Attorney, Agent, or Firm*—George W. Johnston; William H. Epstein; Lewis J. Kreisler

[57] ABSTRACT

The invention relates to conjugates of lipids and basic, membrane disturbing peptides, particularly compounds of the formula $$(R-CONH)_n-R^3 \qquad (I)$$

and $$(R-S-S)_n-R^3 \qquad (II)$$

wherein R is the hydrocarbyl moiety of a straight-chain or branched-chain, saturated or unsaturated aliphatic carboxylic acid, or a phospholipid moiety having a free valence bond; $R^3$ is a basic membrane disturbing peptide having a free valence bond at one or two carbon atom(s); and n is 1 or 2. These conjugates can be used as a vector for transfecting a cell with a polynucleotide or any other anionic macromolecule.

12 Claims, No Drawings

PEPTIDE CONJUGATES FOR TRANSFECTING CELLS

BACKGROUND OF THE INVENTION

Throughout this application the following standard abbreviations are used to refer to amino acids:

| | | |
|---|---|---|
| Alanine | Ala | A |
| Glutamate | Glu | E |
| Glutamine | Gln | Q |
| Aspartate | Asp | D |
| Asparagine | Asn | N |
| Leucine | Leu | L |
| Glycine | Gly | G |
| Lysine | Lys | K |
| Serine | Ser | S |
| Valine | Val | V |
| Arginine | Arg | R |
| Threonine | Thr | T |
| Proline | Pro | P |
| Isoleucine | Ile | I |
| Methionine | Met | M |
| Phenylalanine | Phe | F |
| Tyrosine | Tyr | Y |
| Cysteine | Cys | C |
| Tryptophan | Trp | W |
| Histidine | His | H |
| Ornithine | Orn | |

Gene transfer technology has become a field of considerable interest. Introduction of an exogeneous gene into a cell (i.e. transfection) bears many important scientific and medical applications, going from gene regulation and the production of recombinant proteins to gene therapy.

Viruses have evolved to bypass the different cellular barriers to gene transfer and have indeed become vectors of choice for transfection. Many viruses, including retrovirus, adenovirus or herpes virus, are now engineered to carry therapeutic genes and used in human clinical trials for gene therapy. However, there remains a risk of infectious and immunologic reaction and the large scale production of viruses is difficult and time consuming.

For these various reasons non viral systems have been developed to carry DNA into cells, e.g., the transfection technique based on a cationic lipid, the dioleoyloxypropyl trimethylammonium (Felgner et al., Proc. Natl., Acad. Sci. U.S.A., 84, 7413–7417, 1987) commercialized as Lipofectin™. Since the discovery of this transfection technique, many more cationic lipids have been synthesized and some are commercially available as transfecting reagent for laboratory use: DOGS (Transfectam™), DOSPA (Lipofectamine™), DOTAP (DOTAP™).

Nevertheless, despite important progress in the formulation of non-viral gene delivery systems, there remains a need for more efficient techniques, since the transfection efficiency of synthetic systems is usually below that of viral vectors. Furthermore, many problems still arise in vivo, and the poor stability of the non-viral systems in biological fluids does not allow high and reproducible levels of transfection in vivo.

Cell-lytic antibacterial peptides that act by perturbing the barrier function of membranes are reviewed in Saberwal, et al., Biochim. Biophys. Acta. (1994) 1197:109–131. Certain fatty acid-bearing basic peptides having antibacterial activity are disclosed in Vogler, et al., Helv. Chim. Acta (1964) 47:526–543. Poly(lysine-serine) random polymers for use as carriers to transport oligonucleotides into a cell is disclosed in European Patent Publication No. EP 0 727 223.

SUMMARY OF THE INVENTION

A compound of the formula $(R—CONH)_n—R^3$ (formula I) or $(R—S—S)_n—R^3$ (formula II) wherein R is the hydrocarbyl moiety of a straight-chain or branched-chain, saturated or unsaturated aliphatic carboxylic acid, or a phospholipid moiety; n is 1 or 2; and $R^3$ is a basic membrane disturbing peptide or derivative thereof, wherein $R^3$ contains at least one positively charged amino acid, and is covalently bonded to each R—CONH or R—SS at one carbon atom of $R^3$ when n is 1 or at two carbon atoms of $R^3$ when n is 2.

A composition comprising at least one compound of formula I or I; and from 0.1 nanogram to 1 gram of an anionic macromolecule containing at least one negative charge per molecule, wherein the compound is present in an amount sufficient to provide a positive to negative charge ratio from 0.1 to 10 in the composition.

A composition adapted to deliver to cell from 0.1 nanogram to 1 gram of an anionic macromolecule containing at least one negative charge per molecule, comprising at least one compound of formula I or II.

A method of transfecting a cell with an anionic macromolecule containing at least one negative charge per molecule, comprising contacting the cell with anionic macromolecule in the presence of a compound of formula I or II, so as to transfect the cell with the anionic macromolecule.

In accordance with the present invention it has been found that conjugating a lipid to a basic, membrane disturbing peptide results in novel compounds that bind polynucleotides and other anionic macromolecules and can be used for transfection of cells. Thus, the invention is concerned with compounds which are conjugates of lipids and basic, membrane disturbing peptides and which are transfection competent molecules.

DETAILED DESCRIPTION OF THE INVENTION

In one aspect, the novel compounds of the present invention are compounds of the formula

$$(R—CONH)_n—R^3 \quad\quad I$$

wherein R is the hydrocarbyl moiety of a straight-chain or branched-chain, saturated or unsaturated aliphatic carboxylic acid, or a phospholipid moiety; n is 1 or 2; and $R^3$ is a basic membrane disturbing peptide or derivative thereof, wherein $R^3$ contains at least one positively charged amino acid, and is covalently bonded to each R—CONH at one carbon atom of the $R^3$ group when n is 1 or at two carbon atoms of the $R^3$ group when n is 2.

Preferably, n is 1. Particularly preferred compounds are those of the formula

IA

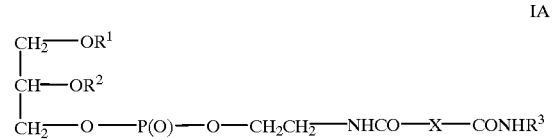

wherein X is $C_{2-10}$ alkylene, $R^1$ and $R^2$ independently are an acyl moiety of a $C_{12-20}$ aliphatic carboxylic acid and $R^3$ is as defined above.

The term "$C_{12-20}$" denotes a number of carbon atoms of from 12 to 20. The acyl moieties $R^1$ and $R^2$ can be a straight-chain or branched-chain, saturated or unsaturated moiety. Examples of such moieties are lauroyl, palmitoyl, stearoyl and oleoyl. In a preferred aspect, $R^1$ and $R^2$ are oleoyl. X is preferably ethylene, propylene or decamethylene.

In another and preferred aspect, the invention relates to novel compounds of the formula

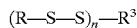   II wherein R is the hydrocarbyl moiety of a straight-chain or branched-chain, saturated or unsaturated aliphatic carboxylic acid, or a phospholipid moiety; n is 1 or 2; and $R^3$ is a basic membrane disturbing peptide or derivative thereof, wherein $R^3$ contains at least one positively charged amino acid, and is covalently bonded to each R—CONH at one carbon atom of the $R^3$ group when n is 1 or at two carbon atoms of the $R^3$ group when n is 2.

R is covalently bonded to —CONH by means of any atom having a free valence bond which is available for bonding to —CONH. $R^3$ is bonded to each R—CONH or R—SS by means of one carbon having a free valence bond available to form such a bond in the case where n=1, and by means of two carbons, each carbon having a free valence bond available to bond to one R—CONH or R—SS moiety. The carbon atoms having the available valence bond, which are the carbon atoms carrying the R—CONH or R—SS moiety, may be any carbon atom in the peptide except the carbonyl carbons. For example, referring to Example 1 below, the peptide prepared in paragraph (a) is a basic membrane-disturbing peptide. By removal of the —SH groups in the Cys residue one obtains a peptide having a free valence bond at one carbon atom, namely at the $C_\beta$ of the Cys residue from which the —SH group has been removed. This free valence bond is available for binding one R moiety (via a —CONH or —SS— bridge).

In the compounds of formula II, n is preferably 1. Most preferred are compounds of the formula

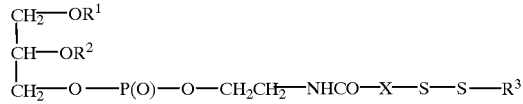   IIA wherein $R^1$, $R^2$, $R^3$ and X are as defined above.

Most preferably $R^3$ is the residue
—(CH$_2$)—CH(NH$_2$)—CO-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-NH$_2$. (SEQ ID No:37)

The compounds of this invention can be used for transfecting cells. Transfection of cells with oligonucleotides such as DNA can be used, for example to express in a host cell or organism, a protein which is not normally expressed by that cell or organism. For example, a self replicating DNA molecule called a plasmid may be introduced into a cell not normally containing that plasmid in order to express a marker gene product in that cell, or to express a protein of interest such as a recombinant protein which is later harvested from such cells. (See Sambrook, et al., Molecular Cloning: A Laboratory Manual, 2nd ed. (Cold Spring Harbor, 1989), ch. 1.) The transfection of oligonucleotides into cells can also be used therapeutically. For example, antisense oligonucleotides, once in the cell or cell nucleus, bind to target single-stranded nucleic acid molecules by Watson-Crick base pairing or to double stranded nucleic acids by Hoogsteen base pairing, and in doing so disrupt the function of the target by one of several mechanisms: by preventing the binding of factors required for normal transcription, splicing, or translation; by triggering the enzymatic degradation of mRNA by RNAse H, or by destroying the target via reactive groups attached directly to the antisense oligonucleotide. (See Zamecnic et al., Proc. Natl. Acad. Sci.-U.S.A. (1978) 75:280–284). Gene therapy or DNA based vaccination are other therapeutic applications.

Proteins and other anionic macromolecules are transferred into cells for therapeutic and screening purposes. For example, immunization is enhanced by introducing an immunogenic protein into a cell, so that it is more efficiently processed and presented on the surface of the cells, thereby enhancing the immunogenic response. Negatively charged anionic macromolecules which act inside a cell are transported past the hydrophobic cell membrane into the cytoplasm where they exert their effect. Factors which enhance or hinder transcription of DNA can be used in a screening test to verify the transcription of a gene of interest. These transcription assays are very well known for use in screening compounds to determine their effect against a particular macromolecule, for example a cell receptor.

The term "conjugates" means compounds consisting of a lipid chemically bound to the peptide, e.g., via a disulfide bond formed between a sulfur atom present in or attached to the lipid and a sulfur atom present in or attached to the peptide; or an amide bond formed between the carboxyl group present in or attached to the lipid and an amino group of the peptide.

The term "lipid" as used herein comprises straight-chain, branched-chain, saturated or unsaturated aliphatic carboxylic acids and phospholipids. Examples of aliphatic carboxylic acids are lauric acid, palmitic acid, stearic acid, oleic acid and $(CH_3(CH_2)_n)_2CH\ COOH$, where n is an integer from 3 to 19. Examples of phospholipids are phosphatidylethanolamines such as dioleoylphosphatidylethanolamine.

The term "basic peptides" denotes peptides containing at least one basic amino acid. Examples of such basic amino acids are natural and unnatural diamino-monocarboxylic acids, such as alpha, beta-diaminopropionic acid, alpha, gamma-diaminobutyric acid, lysine, arginine, ornithine and p-aminophenylalanine.

The term "membrane disturbing peptides" denotes known cell-lytic or antibacterial peptides which perturb the barrier function of membranes (G. Saberwal and R. Nagaraj, Biochim. Biophys. Acta., 1197:109–131, 1994). Examples of basic, cell-lytic peptides are melittin, hemolysin, mastoparan, bombolitin, crabrolin and derivatives or analogs thereof (Saberwal, et al.). Examples of basic antibacterial peptides are cecropins, magainins (Saberwal, et al.), gramicidin S and tyrocidine (Merck Index, 12th ed. 1996, Reg. Nos. 4552 and 9967, respectively) and derivatives or analogs thereof. The term "analogs" refers to peptides wherein one or more amino acid residues are missing or have been replaced by another amino acid residue without substantially changing the biological activity of the original peptide concerned. Such analogs include for example, conservative amino acid substitutions and the specific analogs whose activity is discussed in Saberwal, et al. Examples of known membrane disturbing peptides are shown in Table 1. The term "derivatives" refers to peptides wherein the terminal carboxyl group is esterified, particularly to form lower alkyl esters such as the methyl and ethyl ester; or converted into an amide, lower alkyl amide or di-lower alkyl amide or hydrazide. The term "lower" denotes groups containing from 1–6 carbon atoms.

TABLE 1

| SEQ ID NO. | NAME | SEQUENCE |
|---|---|---|
| 4 | Melittin | GIGAVLKVLTTGLPALISWIKRKRQQ-CONH$_2$ |
| 5 | δ-Hemolysin | (formyl)-MAQDIISTIGDLVKWIIDTVNKFTKK |
| 6 | Mastoparan (*Vespula lewissii*) | INLKALAALAKKIL-CONH$_2$ |
| 7 | Mastoparan (*Vespa vasalis*) | LKLKSIVSWAKKVL-CONH$_2$ |
| | Bombolitin | |
| 8 | I | IKITTMLAKLGKVLAHV-CONH$_2$ |
| 9 | II | SKITDILAKLGKVLAHV-CONH$_2$ |
| 10 | III | IKIMDILAKLGKVLAHV-CONH$_2$ |
| 11 | IV | INIKDILAKLVKVLGHV-CONH$_2$ |
| 12 | V | INVLGILGLLGKALSHL-CONH$_2$ |
| 13 | Crabrolin | FLPLILRKIVTAL-CONH$_2$ |
| 14 | Crabolin-like peptides | FLPAIAGILSQLF-CONH$_2$ |
| 15 | | FLPLIAGLLGKLF-CONH$_2$ |
| | Cecropins | |
| 16 | A | KWKLFKKIEKVGQNIRDGIIKAGPAVAVVGQATQIAK-CONH$_2$ |
| 17 | A (N-terminal K deleted) | WKLFKKIEKVGQNIRDGIIKAGPAVAVVGQATQIAK-CONH$_2$ |
| 18 | A (up to 4 C-terminal residues deleted) | KWKLFKKIEKVGQNIRDGIIKAGPAVAVVGQAT-CONH$_2$ |
| 19 | B | KWKVFKKIEKMGRNIRNGIVKAGPAIAVLGEAKAL-CONH$_2$ |
| 20 | B (N-terminal K deleted) | WKVFKKIEKMGRNIRNGIVKAGPAIAVLGEAKAL-CONH$_2$ |
| 21 | D | WNPFKELEKVGQRVRDAVISAGPAVATVAQATALAK-CONH$_2$ |
| 22 | P1 | SWLSKTAKKLENSAKKRISEGIAIAIQGGPR |
| 23 | Bombyx | RW-KIFKKIEKMGRNIRDGIVKAGPAIEVLGSAKAI-CONH$_2$ |
| 24 | Antheraea | KW-KIFKKIEKVGRNIRNGIIKAGPAVAVLGEAKAL-CONH$_2$ |
| 25 | Hyalophora | FW-KVFKKIEKMGRNIRNGIVKAGPAIAVLGEAKAL-CONH$_2$ |
| 26 | Drosophila | GWLKKIGKKIERVGQHTRDATI-QGLGIAQQAANVAATAR-CONH$_2$ |
| 27 | Porcine | SWLSKTAKKLENSAK-KR-ISEGIAIAIQGGPR |
| | Magainins and related peptides | |
| 28 | Magainin 1 | GIGKFLHSAGKFGKAFVGEIMKS |
| 29 | Magainin 2 | GIGKFLHSAKKFGKAFVGEIMNS |
| 30 | Magainin 2 (up to 3 N-terminal residues deleted) | KFLHSAKKFGKAFVGEIMNS |
| 31 | PGLA | GMASKAGAIAGKIAKVALKAL-CONH$_2$ |
| 32 | XPF | GWASKIGQTLGKIAKVGLKELIQPK |
| 33 | LPF | GWASKIGQTLGKIAKVGLQGLMQPK |
| 34 | CPG | GFGSFLGKALKAALKIGANALGGSPQQ |
| 35 | PGQ | GVLSNVIGYLKKLGTGALNAVLKQ |
| | Gramicidin S | Val-Orn-Leu-D-Phe-Pro<br>\|                   \|<br>Pro-D-Phe-Leu-Orn-Val |
| | Tyrocidine A | Val-Orn-Leu-D-Phe-Pro<br>Tyr-Glu-Asn-D-Phe-Phe |
| | Tyrocidine B | Val-Orn-Leu-D-Phe-Pro<br>Tyr-Glu-Asn-D-Phe-Trp |
| | Tyrocidine C | Val-Orn-Leu-D-Phe-Pro<br>Tyr-Glu-Asn-D-Trp-Trp |

Sources: Saberwal, et al., Biochim, Biophys. Acta (1994) 1197: 109–131, and The Merck Index, 12th ed. (1996): Reg. Nos. 4552 and 9967

In another aspect, this invention relates to a process for preparing the novel compounds defined above, i.e., conjugates of lipids and basic, membrane disturbing peptides, and compositions comprising at least one such compound, a polynucleotide or any other anionic macromolecule, and, optionally, a helper lipid and/or a short chain phospholipid, and/or a cationic lipid or another known transfection competent molecule other than a conjugate of this invention (i.e. a compound of formula I or II). In still another aspect, this invention relates to compositions comprising conjugates of lipids and basic, membrane disturbing peptides and a helper lipid and/or a short chain phospholipid, and/or a cationic lipid or another known transfection competent molecule other than a conjugate of this invention, e.g. a compound of formula I or II. The invention further relates to the use of the novel compounds as a carrier for transfecting a cell with a poly-nucleotide or any other anionic macromolecule.

The compounds provided by this invention can be prepared by reacting a peptide of the formula R$^3$NH$_2$ with a lipid of the formula R—COOH, or a peptide of the formula R$^3$SH with a lipid of the formula R—SY wherein Y is a leaving group such as 2-pyridinethio. These reactions can be carried out in a manner known per se.

Thus, the coupling of peptide of the formula R$^3$NH$_2$ with a lipid of the formula R—COOH can be accomplished by reacting the compounds in a suitable solvent in the presence of a condensation agent such as dicyclohexylcarbodiimide in analogy to methods known for producing peptide bonds.

The reaction of a peptide of the formula $R^3SH$ with a compound of formula R—SY can be carried out in an appropriate solvent or solvent mixture which solubilizes both reactants. The compound of formula R—SY can be dissolved in an organic solvent, e.g., in chloroform. The peptide $R^3SH$ is suitably dissolved in aqueous buffer solution, such as phosphate buffer, that contains an appropriate amount of an water-miscible organic solvent such as acetonitrile to accomplish the formation of a single phase reaction system.

Compounds of the formula R—COOH and R—SY are known or can be prepared by known methods, e.g. as described in Biochim.Biophys.Acta 862, 435–439 (1986). For example, compounds of the formula

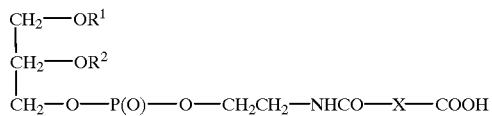

III wherein $R^1$ and $R^2$ are oleolyl, and X is ethylene, propylene or decamethylene and the compound of the formula

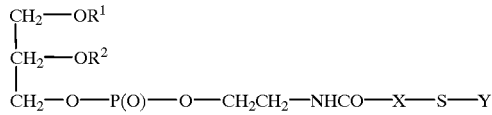

IV wherein $R^1$ and $R^2$ are oleolyl, X is ethylene and Y is 2-pyridinethio are commercially available as N-Succinyl-PE, N-Glutaryl-PE, N-Dodecanyl-PE and N-PDP-PE from Avanti Polar Lipids, Alabaster, Ala., U.S.A.

Any anionic macromolecule can be transfected into a cell using a compound of formula I or II. An anionic macromolecule is a macromolecule which contains at least one negative charge per molecule. Examples of anionic macromolecules which can be transfected in accordance with this invention include polynucleotides, such as deoxyribonucleic acids (DNA) and ribonucleic acids (RNA); and proteins, such as ribonucleoproteins and proteins used for immunization, e.g. viral proteins. Examples of DNA for use in the present invention are plasmids and genes, especially those for which gene therapy protocols have been launched such as cystic fibrosis transmembrane regulator (CFTR), adenosine deaminase (ADA), thymidine kinase (tk) and HLA B7; as well as reporter genes such as beta-galactosidase, luciferase, chloramphenicol transferase and alpha-1 antitrypsin. Other examples of DNA are oligodeoxynucleotides and their analogues used as antisense, aptamer or "triple-helix" agents. Examples of RNA are ribozymes or oligoribonucleotide antisense molecules.

The nature of the cell which is to be transfected is not narrowly crucial. The cell can be a prokaryotic or eukaryotic cell, a mammalian or a plant cell.

In transfecting a cell using a conjugate of this invention, e.g. a compound of formula I or II, the cell is contacted with the anionic macromolecule in the presence of an appropriate amount of such compound. The appropriate amount of the conjugate, e.g. a compound of formula I or II for a given amount of anionic macromolecule depends on their respective charges. The ± charge ratio between the conjugate and the molecule to be transfected generally varies between 0.1–10, preferably between 0.5–5. The value of „± charge ratio" is calculated by dividing the number of positively charged groups on the amino acids in the group $R^3$ by the number of negative charges of the molecule to be transfected. When the molecule to be transfected is a polynucleotide for example, number of negative charges means the number of negatively charged phosphates in the backbone. The optimal ratio within these ranges depends on the cell to be transfected and is readily ascertained by one of skill in the art to which this invention pertains.

The amount of anionic macromolecules to the number of cells is such that the amount of anionic macromolecule for transfecting $10^4$ cells is from 0.1 ng to 10 µg, preferably from 0.2 µg to 2 µg. When the anionic macromolecule is DNA the preferred amount of DNA for transfecting $10^4$ cells in vitro is from 0.1 µg to 10 µg. When cells are being transfected in vivo, the preferred amount of DNA is from 0.1 µg to 1 g.

In a preferred aspect of the invention the transfection is further carried out in the presence of a helper lipid and/or short chain phospholipid, and/or a cationic lipid or any other known transfection competent molecule other than a conjugate of this invention. Any conventional helper lipid can be used. Helper lipids are phospholipids which are known to increase delivery of macromolecules to cells when used together with known transfection competent molecules. Examples of helper lipids are phospholipids, such as phosphatidylcholine or phosphatidylethanolamines or mixtures thereof. Preferred helper lipids are phosphatidylethanolamines, such as dioleoylphosphatidylethanol-amine. Any conventional short chain phospholipid can be used. Short chain phospholipids are phospholipids containing fatty acid residues, which fatty acid residues contain from 6 to 12 carbon atoms in their backbone. Examples of short chain phospholipids are phosphatidylcholines that carry two $C_{6-12}$ fatty acid residues. Preferred short chain phospholipids are dicapryl- and dicapryloyl phosphatidylcholine.

Examples of transfection competent molecules include cationic lipids as described by J. B. Behr in Bioconjugate Chem. 5:382–389 (1994) and X. Gao and L. Huang in Gene Ther. 2:710–722 (1995); polycations as described by A. V. Kabanov and V. A.: Kabanov in Bioconjugate Chem. 6:7–20 (1995); peptides and polymers and other nonviral gene delivery systems as described by F. D. Ledley in Human Gene Therapy 6:1129–1144 (1995).

The helper lipid and/or short chain phospholipid and/or a cationic lipid or another known transfection competent molecule other than a conjugate of this invention is suitably in the form of a liposome, micelles, organic or aqueous dispersions, or organic or aqueous solutions. The optimal molar ratio between the compound of formula I and the helper lipid is 0.1–50, preferably 1–10. The optimal molar ratio between helper lipid and short-chain phospholipid is 2–20. The optimal molar ratio between the compound of formula I or II and additional transfection competent molecules is 0.1–10.

For transfection, an appropriate amount of a conjugate of this invention, e.g., a compound of formula I or II is added to the molecule to be transfected (e.g., plasmid DNA), suitably in an aqueous solution. Optionally, a helper lipid and, if desired, a short chain phospholipid and/or a cationic lipid or another known transfection competent molecule other than a conjugate of this invention is then added, either in form of liposomes, mixed micelles, or as an organic solution or aqueous dispersion. Alternatively, the molecule to be transfected may be added to a composition comprising a compound in accordance with this invention, a helper lipid, and, if desired, a short chain phospholipid and/or a cationic lipid or another known transfection competent molecule other than a conjugate of this invention. The composition may be in solid, liquid, semisolid or aerosol form, suitably in form of liposomes, mixed micelles, or as an organic solution or aqueous dispersion.

For transfecting cells in an animal or human patient the composition can be administered by oral, parenteral (i.v., i.m., s.c., i.d., i.p.) transdermal, pulmonary, nasal, rectal, ocular, ventricular, vascular (catheter) and intratumoral route. Furthermore, the composition can be administered by high velocity impaction administration to the skin surface. The progress of transfection can be measured by appropriate testing protocols which are known to those skilled in the art.

The peptide Cys-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-NH$_2$(SEQ ID NO:36) is novel and is also part of the invention. It can be prepared by methods known in the art, e.g., by solid phase peptide synthesis as described below.

The following examples which are not limitative illustrate the invention further.

EXAMPLE 1 a) Preparation of the Peptide R$^3$S H

Continuous-flow solid-phase synthesis was performed on a Milligen 9050 synthesizer, starting from Tenta Gel S RAM resin (0.22 mmole/g [Rapp Polymere GmbH, Tübingen, Germany] according to the method described by Atherton and Sheppard, Solid Phase Peptide Synthesis: A Practical Approach (IRL Press Oxford 1989). The base-labile Fmoc group was used for a-amino protection. Side chains were protected with the following protection groups: Arg(Pmc), Cys(Trt), Gln(Trt), Lys(Boc), Ser(But) and Trp(Boc). Fmoc-amino acids (2.5 equiv.) were activated with an equivalent amount of TPTU (Knorr et al. Tetrahedron Lett. 1989, 30,1927–1930) and DIPEA. Fmoc deprotection was achieved with 20% piperidine in DMF. (SEQ ID NO:3) Cys(Trt)-Ile-Gly-Ala-Val-Leu-Lys-Val-Leu-Thr(But)-Thr(But)-Gly-Leu-Pro-Ala-Leu-Ile-Ser(But)-Trp(Boc)-Ile-Lys(Boc)Arg(Pmc)-Lys(Boc)Arg(Pmc)-Gln(Trt)-Gln(Trt)-amide Tenta Gel S-resin (1.1 g) was treated with a mixture (20 ml) of 86% TFA, 10% EDT, 4% H$_2$O for 3 hours. The reaction mixture was concentrated and poured into diethyl ether and the precipitate was collected by filtration and lyophilized from water. The crude peptide was purified by preparative HPLC. There was obtained homogenous Cys-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-NH$_2$. 5 TFA. (SEQ ID NO:36)

b) Preparation of a Compound of Formula II

The homogenous peptide obtained in paragraph a) above (34.6 mg, 10 mmole) was dissolved in a mixture of 1 ml of 100 mM phosphate buffer, pH 6.5, and 1 ml of acetonitrile. To this solution there was added 10.6 mg of 1,2-dioleoyl-sn-glycero-3-phosphoethanolamine-N-[3-(2-pyridyldithio) propionate] in 2.8 ml of chloroform. The mixture was left to stand at room temperature for 1 hour and the organic solvent was removed by evaporation. The remaining solution was diluted with water to a volume of 2.5 ml and passed through a Pharmacia Biotech PD-10 column. The product was eluted with 3.5 ml of water and lyophilized. There was obtained 28.9 mg of a the compound of formula IIA wherein R$^1$ and R$^2$ are oleoyl and R$^3$ is the residue —(CH$_2$)—CH(NH$_2$)—CO-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-NH$_2$. (SEQ ID NO:37) ISP-MS:M=3722.

EXAMPLE 2 a) 1.1 mg of the compound obtained in Example 1b) were solubilized in trifluoroethanol and mixed with 1.1 mg of dioleoylphosphatidyl-ethanolamine (DOPE) in chloroform. The mixture was dried in vacuo and the remaining film rehydrated with 1 ml of 30 mM Tris Cl buffer pH 8.5.

b) Plasmid DNA (10 μg) was diluted in 400 μl of 30 mM Tris Cl buffer pH 8.5. Then 20 ml of the product obtain in paragraph a) were added and gently mixed. The mixture was then added to cells.

Table 2 shows the transfection efficiency of the compound obtained in Example 1b formulated according to Example 2 and that of two commercially available transfection vectors, DOTAP and Lipofectamine in various cell lines using the same transfection conditions.

The effect of DNA dose on the transfection efficiency of various cell lines using the compound obtained in Example 1b formulated according to the example 2 is shown in Table 3. The data indicate that high doses of DNA and the compound obtained in Example 1b could be applied on cells without any obvious toxicity.

TABLE 2

Transfection of various cell lines with a mixture of the compound of Example 1b and DOPE or cationic lipids. Cells were transfected with a luciferase encoding plasmid formulated as described earlier in this Example. Luciferase activity was measured 48 h after transfection. Results are expressed as μ Units per well.

| | Luciferase activity | | |
| --- | --- | --- | --- |
| Cell-line | Compound of Example 1b | DOTAP[2] | Lipofectamine 2} |
| 293-EBNA | 2343658 | 706718 | 99050 |
| C2E12 | 563827 | 156947 | 17655 |
| CHO K1 | 1825019 | 814133 | 48457 |
| HeLa | 33497 | 5409 | 243 |
| LM | 31685 | 68614 | 35066 |
| LM tk- | 1712739 | 594518 | 45435 |

[2]DOTAP and Lipofectamine transfection complexes were prepared according to the manufacturer's instructions.

TABLE 3

Transfection of various cell lines with a mixture of the compound of Example 1b and DOPE using increasing DNA doses. Cells were transfected with a β-galactosidase encoding plasmid formulated as described earlier in this Example. β-galactosidase activity was measured 48 h after transfection. Results are expressed as μ Units per well.

| | β-Galactosidase activity | | | |
| --- | --- | --- | --- | --- |
| | COS-1 | HepG2 | CV-1 | 3T3 |
| 0.2 μg DNA | 16325 | 2533 | 2700 | 318 |
| 0.5 μg DNA | 20545 | 7944 | 4440 | 451 |
| 1 μg DNA | 16005 | 8988 | 9775 | 1032 |
| 2 μg DNA | 15740 | 13816 | 20434 | 1301 |

EXAMPLE 3 a) 1.0 mg of the compound obtained in Example 1b) was dissolved in trifluoroethanol and dried in vacuo. The film was then rehydrated with 1 ml of 10 mM Tris maleate buffer pH 6.

b) 10 μl of a plasmid DNA solution (1 mg/ml) were diluted with 190 μl of pure, sterile water. 100 μl of the product obtained in paragraph a) were added and gently mixed. The mixture was then added to cells.

Table 4 shows the transfection efficiency of the compound of Example 1b formulated as described above and that of two commercially available cationic lipid transfection reagents, DOTAP and DOSPER in various cell lines using the same transfection conditions. The data indicate that the compound of Example 1b mediated 3 to 40 and 25 to 500 times greater luciferase activity than DOSPER and DOTAP, respectively. Moreover, only the compound of Example 1b was able to transfect the suspension cell-line WEHI 231.7, albeit at a low level.

Table 4: Transfection of various cell lines with the compound of Example 1b or cationic lipids. Cells grown in 6 well plates were transfected with a luciferase encoding plasmid (2 μg DNA per well) formulated as described earlier in this Example. Luciferase activity was measured 48 h later. Results are expressed as light units per mg of cell protein. Background was substracted from each measurement.

TABLE 4

Transfection of various cell lines with the compound of Example 1b or cationic lipids. Cells grown in 6 well plates were transfected with a luciferase encoding plasmid (2 μg DNA per well) formulated as described earlier in this Example. Luciferase activity was measured 48 h later. Results are expressed as light units per mg of cell protein. Background was substracted from each measurement.

| Cell line | Luciferase activity | | |
|---|---|---|---|
|  | DOTAP* | DOSPER* | Compound of Example 1b |
| CHO-K1 | $2.69 \; 10^6$ | $2.50 \; 10^7$ | $5.19 \; 10^8$ |
| CV-1 | $1.14 \; 10^5$ | $1.31 \; 10^6$ | $5.54 \; 10^7$ |
| 293 | $7.31 \; 10^6$ | $5.70 \; 10^7$ | $1.71 \; 10^8$ |
| WEHI 231.7 | 0 | 0 | $1.85 \; 10^2$ |

*)DOTAP (Avanti Polar Lipids Inc.) or DOSPER (Boehringer-Mannheim) transfection complexes were prepared according to manufacturer's instructions and were used at a cationic lipid/DNA ratio of 5/1 (wt/wt).

EXAMPLE 4 a) 1.0 mg of the compound obtained in Example 1b) was dissolved in trifluoroethanol and dried in vacuo. The film was then rehydrated with 1 ml of 10 mM Tris maleate buffer pH 6.

b) 10 μl of a plasmid DNA solution (1 mg/ml) were diluted with 200 μl of pure, sterile water. 39 μl of the product obtained in paragraph a) and 14 μl of an aqueous polyethylenimine solution (0.45 mg/ml) were added. The mixture was adjusted with water to 300 μl, gently mixed and then added to 292 EBNA cells.

c) 10 μl of a plasmid DNA solution (1 mg/ml) were diluted with 200 μl of pure, sterile water. 52 μl of the product obtained in paragraph a) were added and adjusted with water to 300 μl. The mixture was gently mixed and then added to 292 EBNA cells.

d) 10 μl of a plasmid DNA solution (1 mg/ml) were diluted with 200 μl of pure, sterile water. 56 μl of an aqueous polyethylenimine solution (0.45 mg/ml) were added and adjusted with water to 300 μl. The mixture was gently mixed and then added to 292 EBNA cells.

Table 4 shows the transfection efficiency of the compound of Example 1b, polyethylenimine and a mixture thereof formulated earlier in this Example. The data indicate that the mixture mediated 250 and 25 times greater luciferase activity than compound of Example 1b and polyethylenimine, respectively.

TABLE 5

Transfection of 293 EBNA cells with the compound of Example 1b, polyethylenimine or a mixture thereof. Cells grown in 6 cm dishes were transfected with a luciferase encoding plasmid (1 μg DNA per well) formulated as described earlier in this Example. Luciferase activity was measured 48 h later. Results are expressed as relative light units per dish.

| Transfection agent | Luciferase activity |
|---|---|
| Compound of Example 1b | $3.9 \times 10^5$ |
| Polyethylenimine | $3.8 \times 10^4$ |
| Compound of Example 1b/ Polyethylenimine | $9.8 \times 10^6$ |

What is claimed is:

1. A peptide, Cys-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-NH$_2$ (SEQ ID NO:36) and derivatives thereof wherein the amino groups are protected.

2. A compound of the formula

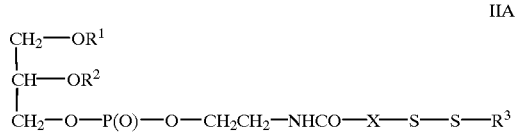

IIA wherein X is C$_{2-10}$ alkylene; R$^1$ and R$^2$ are oleoyl; and R$^3$ is —CH$_2$)—CH(NH$_2$)—CO-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-NH$_2$ (SEQ ID NO:37).

3. A compound of the formula

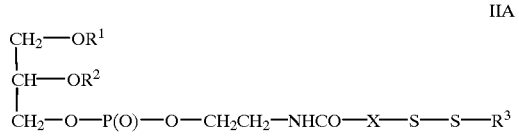

IIA wherein X is C$_{2-10}$ alkylene; R$^1$ and R$^2$ are independently an acyl moiety of a C$_{12-20}$ aliphatic carboxylic acid; and R$^3$ is —(CH$_2$)—CH(NH$_2$)—CO-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln-NH$_2$ (SEQ ID NO:37).

4. A composition comprising at least one compound of claim 3; and from 0.1 nanogram to 1 gram of an anionic macromolecule containing at least one negative charge per molecule, wherein the compound is present in an amount sufficient to provide a positive to negative charge ratio from 0.1 to 10 in the composition.

5. The composition of claim 4, further comprising one or more of the group consisting of a helper lipid, a short chain phospholipid, a cationic lipid, and a known transfection competent molecule other than the compound.

6. The composition of claim 4 wherein the anionic macromolecule is a polypeptide.

7. The composition of in claim 4 wherein the composition is in the form of an aqueous or organic solution, an aqueous or organic dispersion, or a liposome or a micelle.

8. The composition of claim 4 wherein the composition is in solid, liquid, semisolid or aerosol form.

9. A composition adapted to deliver to a cell from 0.1 nanogram to 1 gram of an anionic macromolecule containing at least one negative charge per molecule, comprising at least one compound of claim 3.

10. The composition of claim 9, further comprising one or more of a helper lipid, a short chain phospholipid, a cationic lipid, and a known transfection competent molecule other than the compound.

11. The composition of claim 9 wherein the composition is in the form of an aqueous or organic solution, an aqueous or organic dispersion, or a liposome or a micelle.

12. The composition of claim 9, wherein the composition is in the form of an aqueous or organic solution, an aqueous or organic dispersion, or a liposome or a micelle.

* * * * *

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
      (A) LENGTH: 25 amino acids
      (B) TYPE: amino acid
      (D) TOPOLOGY: linear (ii) MOLECULE TYPE: peptide (iii) HYPOTHETICAL: NO (xi) SEQUENCE DESCRIPTION: SEQ ID NO:1:

```
Gln Gln Arg Lys Arg Lys Ile Trp Ser Ile Leu Ala Pro Leu Gly Thr
 1               5                  10                  15

Thr Leu Val Lys Leu Val Ala Gly Ile
                20              25
```

(2) INFORMATION FOR SEQ ID NO:2:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:2:

```
Gln Gln Arg Lys Arg Lys Ile Trp Ser Ile Leu Ala Pro Leu Gly Thr
 1               5                  10                  15

Thr Leu Val Lys Leu Val Ala Gly Ile Cys
                20              25
```

(2) INFORMATION FOR SEQ ID NO:3:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (iii) HYPOTHETICAL: NO (ix) FEATURE:
        (A) NAME/KEY: Modified-site
        (B) LOCATION: 1..26
        (D) OTHER INFORMATION: /note= "1Cys(Trt), 10Thr(But),
            11Thr(But), 18Ser(But), 19Trp(Boc), 21Lys(Box),
            22Arg(Pmc), 23Lys(Boc), 24Arg(Pmc), 25Gln(Trt), (xi) SEQUENCE DESCRIPTION: SEQ ID NO:3:

```
Cys Ile Gly Ala Val Leu Lys Val Leu Thr Thr Gly Leu Pro Ala Leu
 1               5                  10                  15

Ile Ser Trp Ile Lys Arg Lys Arg Gln Gln
                20              25
```

(2) INFORMATION FOR SEQ ID NO:4:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:4:

```
Gly Ile Gly Ala Val Leu Lys Val Leu Thr Thr Gly Leu Pro Ala Leu
 1               5                  10                  15

Ile Ser Trp Ile Lys Arg Lys Arg Gln Gln
                20              25
```

(2) INFORMATION FOR SEQ ID NO:5:

(i) SEQUENCE CHARACTERISTICS:
        (A) LENGTH: 26 amino acids
        (B) TYPE: amino acid (D) TOPOLOGY: linear (ii) MOLECULE TYPE: peptide (iii) HYPOTHETICAL: NO (ix) FEATURE:
            (A) NAME/KEY: Modified-site
            (B) LOCATION: 1..2
            (D) OTHER INFORMATION: /note= "Position 1 is fMet."

(xi) SEQUENCE DESCRIPTION: SEQ ID NO:5:

Met Ala Gln Asp Ile Ile Ser Thr Ile Gly Asp Leu Val Lys Trp Ile
1               5                   10                  15

Ile Asp Thr Val Asn Lys Phe Thr Lys Lys
                20                  25

(2) INFORMATION FOR SEQ ID NO:6:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (iii) HYPOTHETICAL: NO (xi) SEQUENCE DESCRIPTION: SEQ ID NO:6:

Ile Asn Leu Lys Ala Leu Ala Ala Leu Ala Lys Lys Ile Leu
1               5                   10

(2) INFORMATION FOR SEQ ID NO:7:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (iii) HYPOTHETICAL: NO (xi) SEQUENCE DESCRIPTION: SEQ ID NO:7:

Leu Lys Leu Lys Ser Ile Val Ser Trp Ala Lys Lys Val Leu
1               5                   10

(2) INFORMATION FOR SEQ ID NO:8:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (iii) HYPOTHETICAL: NO (xi) SEQUENCE DESCRIPTION: SEQ ID NO:8:

Ile Lys Ile Thr Thr Met Leu Ala Lys Leu Gly Lys Val Leu Ala His
1               5                   10                  15

Val (2) INFORMATION FOR SEQ ID NO:9:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (iii) HYPOTHETICAL: NO (xi) SEQUENCE DESCRIPTION: SEQ ID NO:9:

Ser Lys Ile Thr Asp Ile Leu Ala Lys Leu Gly Lys Val Leu Ala His
1               5                   10                  15
Val (2) INFORMATION FOR SEQ ID NO:10:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (iii) HYPOTHETICAL: NO (xi) SEQUENCE DESCRIPTION: SEQ ID NO:10:

Ile Lys Ile Met Asp Ile Leu Ala Lys Leu Gly Lys Val Leu Ala His
1               5                   10                  15
Val (2) INFORMATION FOR SEQ ID NO:11:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (iii) HYPOTHETICAL: NO (xi) SEQUENCE DESCRIPTION: SEQ ID NO:11:

Ile Asn Ile Lys Asp Ile Leu Ala Lys Leu Val Lys Val Leu Gly His
1               5                   10                  15
Val (2) INFORMATION FOR SEQ ID NO:12:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (iii) HYPOTHETICAL: NO (xi) SEQUENCE DESCRIPTION: SEQ ID NO:12:

Ile Asn Val Leu Gly Ile Leu Gly Leu Leu Gly Lys Ala Leu Ser His
1               5                   10                  15
Leu (2) INFORMATION FOR SEQ ID NO:13:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (iii) HYPOTHETICAL: NO (xi) SEQUENCE DESCRIPTION: SEQ ID NO:13:

Phe Leu Pro Leu Ile Leu Arg Lys Ile Val Thr Ala Leu
1               5                   10

(2) INFORMATION FOR SEQ ID NO:14:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (iii) HYPOTHETICAL: NO (xi) SEQUENCE DESCRIPTION: SEQ ID NO:14:

Phe Leu Pro Ala Ile Ala Gly Ile Leu Ser Gln Leu Phe
1               5                   10

(2) INFORMATION FOR SEQ ID NO:15:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (iii) HYPOTHETICAL: NO (xi) SEQUENCE DESCRIPTION: SEQ ID NO:15:

Phe Leu Pro Leu Ile Ala Gly Leu Leu Gly Lys Leu Phe
1               5                   10

(2) INFORMATION FOR SEQ ID NO:16:

(i) SEQUENCE CHARACTERISTICS:
            (A) LENGTH: 37 amino acids
            (B) TYPE: amino acid
            (D) TOPOLOGY: linear (ii) MOLECULE TYPE: peptide (iii) HYPOTHETICAL: NO (xi) SEQUENCE DESCRIPTION: SEQ ID NO:16:

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
                20                  25                  30

Thr Gln Ile Ala Lys
            35

(2) INFORMATION FOR SEQ ID NO:17:

(i) SEQUENCE CHARACTERISTICS:
            (A) LENGTH: 36 amino acids
            (B) TYPE: amino acid
            (D) TOPOLOGY: linear (ii) MOLECULE TYPE: peptide (iii) HYPOTHETICAL: NO (xi) SEQUENCE DESCRIPTION: SEQ ID NO:17:

Trp Lys Leu Phe Lys Lys Ile Glu Lys Val Gly Gln Asn Ile Arg Asp

```
                1               5              10              15
Gly Ile Ile Lys Ala Gly Pro Ala Val Ala Val Val Gly Gln Ala Thr
                20              25              30
Gln Ile Ala Lys
        35

(2) INFORMATION FOR SEQ ID NO:18:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:18:

Lys Trp Lys Leu Phe Lys Lys Ile Glu Lys Val Gly Gln Asn Ile Arg
1               5              10              15
Asp Gly Ile Ile Lys Ala Gly Pro Ala Val Ala Val Val Gly Gln Ala
                20              25              30
Thr (2) INFORMATION FOR SEQ ID NO:19:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:19:

Lys Trp Lys Val Phe Lys Lys Ile Glu Lys Met Gly Arg Asn Ile Arg
1               5              10              15
Asn Gly Ile Val Lys Ala Gly Pro Ala Ile Ala Val Leu Gly Glu Ala
                20              25              30
Lys Ala Leu
        35

(2) INFORMATION FOR SEQ ID NO:20:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:20:

Trp Lys Val Phe Lys Lys Ile Glu Lys Met Gly Arg Asn Ile Arg Asn
1               5              10              15
Gly Ile Val Lys Ala Gly Pro Ala Ile Ala Val Leu Gly Glu Ala Lys
                20              25              30
Ala Leu (2) INFORMATION FOR SEQ ID NO:21:

(i) SEQUENCE CHARACTERISTICS:
```

(A) LENGTH: 36 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:21:

Trp Asn Pro Phe Lys Glu Leu Glu Lys Val Gly Gln Arg Val Arg Asp
1               5                  10                  15

Ala Val Ile Ser Ala Gly Pro Ala Val Ala Thr Val Ala Gln Ala Thr
            20                  25                  30

Ala Leu Ala Lys
        35

(2) INFORMATION FOR SEQ ID NO:22:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:22:

Ser Trp Leu Ser Lys Thr Ala Lys Lys Leu Glu Asn Ser Ala Lys Lys
1               5                  10                  15

Arg Ile Ser Glu Gly Ile Ala Ile Ala Ile Gln Gly Gly Pro Arg
            20                  25                  30

(2) INFORMATION FOR SEQ ID NO:23:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:23:

Arg Trp Lys Ile Phe Lys Lys Ile Glu Lys Met Gly Arg Asn Ile Arg
1               5                  10                  15

Asp Gly Ile Val Lys Ala Gly Pro Ala Ile Glu Val Leu Gly Ser Ala
            20                  25                  30

Lys Ala Ile
        35

(2) INFORMATION FOR SEQ ID NO:24:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:24:

Lys Trp Lys Ile Phe Lys Lys Ile Glu Lys Val Gly Arg Asn Ile Arg
1               5                  10                  15

```
Asn Gly Ile Ile Lys Ala Gly Pro Ala Val Ala Val Leu Gly Glu Ala
            20                  25                  30

Lys Ala Leu
        35

(2) INFORMATION FOR SEQ ID NO:25:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:25:

Phe Trp Lys Val Phe Lys Lys Ile Glu Lys Met Gly Arg Asn Ile Arg
1               5                   10                  15

Asn Gly Ile Val Lys Ala Gly Pro Ala Ile Ala Val Leu Gly Glu Ala
            20                  25                  30

Lys Ala Leu
        35

(2) INFORMATION FOR SEQ ID NO:26:

(i) SEQUENCE CHARACTERISTICS:
        (A) LENGTH: 39 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:26:

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg
        35

(2) INFORMATION FOR SEQ ID NO:27:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:27:

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

(2) INFORMATION FOR SEQ ID NO:28:

(i) SEQUENCE CHARACTERISTICS:
        (A) LENGTH: 23 amino acids
        (B) TYPE: amino acid
        (D) TOPOLOGY: linear
```

(ii) MOLECULE TYPE: peptide (iii) HYPOTHETICAL: NO (xi) SEQUENCE DESCRIPTION: SEQ ID NO:28:

Gly Ile Gly Lys Phe Leu His Ser Ala Gly Lys Phe Gly Lys Ala Phe
1               5                  10                  15

Val Gly Glu Ile Met Lys Ser
            20

(2) INFORMATION FOR SEQ ID NO:29:

(i) SEQUENCE CHARACTERISTICS:
            (A) LENGTH: 23 amino acids
            (B) TYPE: amino acid
            (D) TOPOLOGY: linear (ii) MOLECULE TYPE: peptide (iii) HYPOTHETICAL: NO (xi) SEQUENCE DESCRIPTION: SEQ ID NO:29:

Gly Ile Gly Lys Phe Leu His Ser Ala Lys Lys Phe Gly Lys Ala Phe
1               5                  10                  15

Val Gly Glu Ile Met Asn Ser
            20

(2) INFORMATION FOR SEQ ID NO:30:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (iii) HYPOTHETICAL: NO (xi) SEQUENCE DESCRIPTION: SEQ ID NO:30:

Lys Phe Leu His Ser Ala Lys Lys Phe Gly Lys Ala Phe Val Gly Glu
1               5                  10                  15

Ile Met Asn Ser
            20

(2) INFORMATION FOR SEQ ID NO:31:

(i) SEQUENCE CHARACTERISTICS:
            (A) LENGTH: 21 amino acids
            (B) TYPE: amino acid
            (D) TOPOLOGY: linear (ii) MOLECULE TYPE: peptide (iii) HYPOTHETICAL: NO (xi) SEQUENCE DESCRIPTION: SEQ ID NO:31:

Gly Met Ala Ser Lys Ala Gly Ala Ile Ala Gly Lys Ile Ala Lys Val
1               5                  10                  15

Ala Leu Lys Ala Leu
            20

(2) INFORMATION FOR SEQ ID NO:32:

(i) SEQUENCE CHARACTERISTICS:
            (A) LENGTH: 25 amino acids
            (B) TYPE: amino acid (D) TOPOLOGY: linear (ii) MOLECULE TYPE: peptide (iii) HYPOTHETICAL: NO (xi) SEQUENCE DESCRIPTION: SEQ ID NO:32:

Gly Trp Ala Ser Lys Ile Gly Gln Thr Leu Gly Lys Ile Ala Lys Val
1               5                   10                  15

Gly Leu Lys Glu Leu Ile Gln Pro Lys
            20                  25

(2) INFORMATION FOR SEQ ID NO:33:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:33:

Gly Trp Ala Ser Lys Ile Gly Gln Thr Leu Gly Lys Ile Ala Lys Val
1               5                   10                  15

Gly Leu Gln Gly Leu Met Gln Pro Lys
            20                  25

(2) INFORMATION FOR SEQ ID NO:34:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:34:

Gly Phe Gly Ser Phe Leu Gly Lys Ala Leu Lys Ala Ala Leu Lys Ile
1               5                   10                  15

Gly Ala Asn Ala Leu Gly Gly Ser Pro Gln Gln
            20                  25

(2) INFORMATION FOR SEQ ID NO:35:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:35:

Gly Val Leu Ser Asn Val Ile Gly Tyr Leu Lys Lys Leu Gly Thr Gly
1               5                   10                  15

Ala Leu Asn Ala Val Leu Lys Gln
            20

(2) INFORMATION FOR SEQ ID NO:36:

(i) SEQUENCE CHARACTERISTICS:
        (A) LENGTH: 26 amino acids

```
            (B) TYPE: amino acid
            (D) TOPOLOGY: linear (ii) MOLECULE TYPE: peptide (iii) HYPOTHETICAL: NO (xi) SEQUENCE DESCRIPTION: SEQ ID NO:36:

Cys Ile Gly Ala Val Leu Lys Val Leu Thr Thr Gly Leu Pro Ala Leu
1               5                   10                  15

Ile Ser Trp Ile Lys Arg Lys Arg Gln Gln
                20                  25

(2) INFORMATION FOR SEQ ID NO:37:

(i) SEQUENCE CHARACTERISTICS:
            (A) LENGTH: 26 amino acids
            (B) TYPE: amino acid
            (D) TOPOLOGY: linear (ii) MOLECULE TYPE: peptide (iii) HYPOTHETICAL: NO (ix) FEATURE:
            (A) NAME/KEY: Modified-site
            (B) LOCATION: 1
            (D) OTHER INFORMATION: /note= "1Cys -SH has been removed (xi) SEQUENCE DESCRIPTION: SEQ ID NO:37:

Cys Ile Gly Ala Val Leu Lys Val Leu Thr Thr Gly Leu Pro Ala Leu
1               5                   10                  15

Ile Ser Trp Ile Lys Arg Lys Arg Gln Gln
                20                  25
```